United States Patent
Zhang et al.

(10) Patent No.: US 8,496,800 B2
(45) Date of Patent: Jul. 30, 2013

(54) USE OF POLYOXYALKYLENE NONIONIC SURFACTANTS WITH MAGNESIUM ION SELECTIVE ELECTRODES

(75) Inventors: Wei Zhang, Norwood, MA (US); Kevin Horan, Raynham, MA (US); Laura S. Uretsky, Milford, MA (US)

(73) Assignee: Siemens Healthcare Diagnostics Inc., Tarrytown, NY (US)

( * ) Notice: Subject to any disclaimer, the term of this patent is extended or adjusted under 35 U.S.C. 154(b) by 274 days.

(21) Appl. No.: 13/059,671

(22) PCT Filed: Aug. 14, 2009

(86) PCT No.: PCT/US2009/053840
§ 371 (c)(1),
(2), (4) Date: Feb. 18, 2011

(87) PCT Pub. No.: WO2010/021923
PCT Pub. Date: Feb. 25, 2010

(65) Prior Publication Data
US 2011/0139638 A1    Jun. 16, 2011

Related U.S. Application Data

(60) Provisional application No. 61/090,671, filed on Aug. 21, 2008.

(51) Int. Cl.
*G01N 27/333* (2006.01)
(52) U.S. Cl.
USPC ................ 205/789.5; 204/416; 204/418
(58) Field of Classification Search
USPC ................ 204/416–419; 205/781.5
See application file for complete search history.

(56) References Cited

U.S. PATENT DOCUMENTS

| | | | |
|---|---|---|---|
| 5,154,850 A | * | 10/1992 | Deguchi et al. ............... 510/420 |
| 6,150,128 A | | 11/2000 | Uretsky |
| 7,820,745 B2 | * | 10/2010 | Kashiwagi ..................... 524/111 |

FOREIGN PATENT DOCUMENTS

| | | | |
|---|---|---|---|
| JP | 2006-300587 A | * | 11/2006 |
| JP | 2007-071792 A | * | 3/2007 |

OTHER PUBLICATIONS

JPO computer-generated English language translation of Claims and Description of Fujimori JP 2006-300587 A , patent published Nov. 2, 2006.*
JPO computer-generated English language translation of Claims and Description of Yamasato et al. JP 2007-071792 A , patent published Mar. 22, 2007.*
Table of polyoxyethylene sorbitan fatty acid esters (general use) offered by Kao Global Chemicals downloaded on Jan. 10, 2013 from http://chemical.kao.com/global/products/class/c020806.html.*

(Continued)

*Primary Examiner* — Alex Noguerola
(74) *Attorney, Agent, or Firm* — Noam R. Pollack

(57) ABSTRACT

Methods are disclosed for reducing the shift in EMF bias in a magnesium ion selective electrode, comprising the step of: contacting the electrode with a composition comprising a polyoxyalkylene nonionic surfactant; wherein the polyoxyalkylene nonionic surfactant has an HLB greater than about 18. Additional aspects of the present invention are directed to methods, comprising the steps of: contacting a magnesium ion selective electrode with a composition comprising a polyoxyalkylene nonionic surfactant, wherein the polyoxyalkylene nonionic surfactant has an HLB greater than about 18; and measuring a biologically relevant level of a blood electrolyte in a blood composition with the electrode. In certain embodiments, the polyoxyalkylene nonionic surfactant is polyoxyethylene (100) stearyl ether and the blood electrolyte is magnesium ion.

35 Claims, 5 Drawing Sheets

OTHER PUBLICATIONS

Able of polyoxyethylene fatty acid esters offered by Kao Global Chemicals downloaded on Jan. 10, 2013 from http://chemical.kao.com/sg/products/class/c020812.html.*

Product Identification (description of and listing of properties) for octylphenol ethoxylate (polyoxyethylene octyl phenyl ether) by Chemicaland21 downloaded from http://chemicalland21.com/specialtychem/perchem/OCTYLPHENOL%20ETHOXYLATE.htm on Jan. 10, 2013.*

International Search Report and Written Opinion of International Application No. PCT/US2009/053840 mailed on Oct. 6, 2009.

Chaniotakis et al., "Magnesium Ion-Selective Electrode: Optimization and Flow Injection Analysis Application", Dec. 10, 1997, Elsevier—Analytica Chimica Acta 356, pp. 105-111.

Oakton, "Operating Instructions—ION 5 and ION 6 Acorn Series Meters", Aug. 1999, pp. 1-12.

Vaughn M. Nace, "Nonionic Surfactants—Polyoxyalkylene Block Copolymers", 1996, Marcel Dekker, Inc., pp. 1-30.

Meziani et al., "Comparison of Enzymatic Activity and Nanostructures in Water/Ethanol/Brij 35 and Water/1-Pentanol/Brij 35 Systems", 1997 American Chemical Society, J. Phys. Chem. B 1997, 101, pp. 3620-3625.

Malinowska et al., "Potentiometric Response of Magnesium-Selective Membrane Electrode in the Presence of Nononic Surfactants", 1999 Elsevier Science—Analytica Chimica Acta 382 (1999), pp. 265-275.

Rayana et al., "Guidelines for Sampling, Measuring and Reporting Ionized Magnesium in Undiluted Serum, Plasma or Blood", 2005, International Federation of Clinical Chemistry and Laboratory Medicine (IFCC), 43 (5): pp. 564-569.

McCaffrey et al., "Clinically Useful Biosensor Membrane Development", 1996, Biofunctional Membranes, Plenum Press, NY, pp. 45-69.

* cited by examiner

US 8,496,800 B2

USE OF POLYOXYALKYLENE NONIONIC SURFACTANTS WITH MAGNESIUM ION SELECTIVE ELECTRODES

This application is a National Stage entry of International Patent Application No. PCT/US2009/053840 filed on Aug. 14, 2009 and claims priority under 35 U.S.C. 119(e) to U.S. Provisional Application No. 61/090,671, filed Aug. 21, 2008, the entire contents of each of which are hereby expressly incorporated herein by reference.

FIELD OF THE INVENTION

The present invention relates to ion selective electrodes, and, in particular, to methods of reducing the shift in EMF bias in a magnesium ion selective electrode.

BACKGROUND OF THE INVENTION

The use of ion selective electrodes (ISEs) to determine the presence and quantity of various analytes in biological samples has become a useful diagnostic technique. Indeed, ISEs have been used to detect analytes such as magnesium, sodium, potassium, calcium, and chloride, among others. Some of these ISEs are often housed within clinical diagnostic instruments for simultaneous analysis of a large number of analytes.

For several reasons, surfactants are often included in reagents used during the operation of ISEs. Various surfactants may be used for this purpose; however, the utility of the surfactant is highly dependent upon the ISEs membrane. For example, an unsuitable surfactant can result in a shift in electromotive force (EMF) bias that does not allow the electrode to measure a biologically relevant amount of an analyte. Further, for electrodes housed within a clinical diagnostic instrument, it is preferred that the surfactant used in the reagents for multiple ISEs is the same or similar. This reduces costs and the potential for contamination.

Issues associated with surfactant selection have led to difficulty in incorporating magnesium ISEs into clinical diagnostic instruments. Alkyl-N-methylglucamide-based nonionic surfactants, such as N-methyl-noctanoyl-D-glucamine (sold under the tradename MEGA 8) or N-methyl-N-nonanoyl-D-glucamine (sold under the tradename MEGA 9), are recommended by IFCC guidelines used in reagents for magnesium ion selective electrodes. Although these surfactants are suitable for use with magnesium ion selective electrodes, they have significant drawbacks. First, the costs of these surfactants are extremely high. Further, these surfactants have a high critical micelle concentration (CMC), requiring a higher concentration of the surfactant in the reagent.

Because of the prohibitive cost of these surfactants, less expensive surfactants are desirable to use in these reagents. When used with magnesium ion selective electrodes, these less expensive surfactants make the electrode inoperable. As such, magnesium ion selective electrodes have only very rarely been included in clinical diagnostic instruments.

Accordingly, a surfactant that does not lead to an unacceptable EMF shift bias when used with a magnesium ISE, that is less expensive than traditional surfactants used with magnesium ISEs, and that may be used as a surfactant for other electrodes within a clinical diagnostic instrument would be highly desirable. The methods and kits of the present invention are directed toward these, as well as other, important ends.

SUMMARY OF THE INVENTION

Aspects of the present invention are directed to methods of reducing the shift in EMF bias in a magnesium ion selective electrode, comprising the step of contacting the electrode with a composition comprising a polyoxyalkylene nonionic surfactant, wherein the polyoxyalkylene nonionic surfactant has an HLB greater than about 18. In certain embodiments, the polyoxyalkylene nonionic surfactant is polyoxyethylene (100) stearyl ether.

Additional aspects of the present invention are directed to methods, comprising the steps of contacting a magnesium ion selective electrode with a composition comprising a polyoxyalkylene nonionic surfactant, wherein the polyoxyalkylene nonionic surfactant has an HLB greater than about 18; and measuring a biologically relevant level of a blood electrolyte in a blood composition with the electrode. In certain embodiments, the polyoxyalkylene nonionic surfactant is polyoxyethylene (100) stearyl ether. In certain embodiments, the blood electrolyte is magnesium ion.

Kits are also described comprising a magnesium ion selective electrode; a calibration reagent, a wash reagent, and slope reagent as well as quality control (QC) materials. All reagents may comprise a polyoxyalkylene nonionic surfactant, wherein the polyoxyalkylene nonionic surfactant has an HLB greater than about 18. The kits may also comprise instructions for rinsing, calibrating, and operating the electrode.

BRIEF DESCRIPTION OF THE DRAWINGS

The accompanying drawings, which are included to provide a further understanding of the invention and are incorporated in and constitute a part of this specification, illustrate embodiments of the invention and together with the description serve to explain the principles of the invention. In the drawings.

DETAILED DESCRIPTION OF ILLUSTRATIVE EMBODIMENTS

Figure 1:
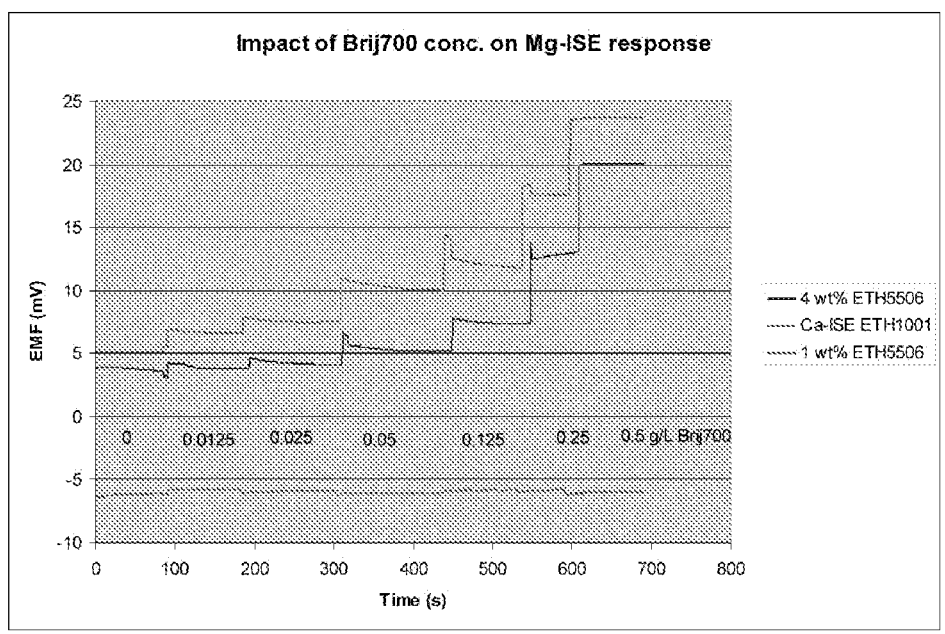
FIG. 1 shows the influence of polyoxyethylene(100) stearyl ether nonionic surfactant (sold under the tradename BRIJ-700®; CAS No. 9005-00-9) on Mg-ISE and Ca-ISE response performances.

Surfactants are often included in ISE reagents for several reasons. These reasons include: to clean the instrument fluidic and measurement systems, to maintain the pliability of the electrode's membrane, and to optimize the instrument's and electrode's performance, among others. When choosing a surfactant for a specific electrode, it is important to recognize that a single surfactant may not be suitable for all types of ISEs. For example, if a particular surfactant produces an EMF shift bias that is too high to detect the analyte of interest, that surfactant may not be desirable.

Choosing a suitable surfactant has been particularly difficult for magnesium ISEs, especially when the electrode is used to analyze magnesium ion content in biological samples. Indeed, drastic interference in Mg-ISE performance has been reported when poly(ethylene oxide) type surfactants are used. E. Malinowska, A. Manzoni, M. Meyerhoff. *Anal. Chim. Acta* 382 (1999) p. 265-275. This interference can be seen by either an unacceptable shift in EMF, or a loss of selectivity of Mg ions over background electrolytes. Indeed, the International Federation of Clinical Chemistry and Laboratory Medicine (IFCC) published guidelines recommending to avoid using poly(ethylene oxide) type surfactants for Mg-ISEs in blood analyzers. IFCC Scientific Division, Committee on Point of Care Testing. *Clin. Chem. Lab Med* 2005:43(5) p. 564-569. These findings and recommendations have made it impractical to analyze biological samples for magnesium ion in a clinical diagnostics instrument because poly(ethylene oxide) type surfactant are often used in reagents for clinical diagnostic instruments.

An additional difficulty when measuring magnesium ion in the presence of background electrolytes is a loss of selectivity over major background electrolytes such as $Ca^{2+}$ and $Na^+$. Unlike with other analytes wherein the use of an unsuitable surfactant results in a gradual decrease in precision and accuracy, the use of an unsuitable surfactant, such as t-octylphenoxypolyethoxyethanol (such as surfactants sold under the tradename TRITON X-100) and polyoxyethylene 23 lauryl ether (such as surfactants sold under the tradename BRIJ-35), results in an immediate reduction in the ability of the Mg-ISE to detect magnesium ions.

Surfactants such as N-methyl-noctanoyl-D-glucamine (MEGA 8) and N-methyl-N-nonanoyl-D-glucamine (MEGA 9) have been disclosed as suitable surfactants for magnesium ISEs. These surfactants, however, are not ideal. First, they are very expensive. Further, they have a high CMC value (MEGA 8~58 mM and MEGA 9~19-25 mM). This high CMC requires a greater concentration of the MEGAs in the reagent.

Aspects of the present invention are directed to methods of reducing the shift in EMF bias in a magnesium ion selective electrode. Methods may comprise the step of contacting a magnesium ion selective electrode with a composition comprising a polyoxyalkylene nonionic surfactant, wherein the polyoxyalkylene nonionic surfactant has an HLB greater than about 18.

Suitable polyoxyalkylene nonionic surfactants may be a polyoxyethylene nonionic surfactant. In some embodiments, the polyoxyethylene nonionic surfactant may be polyoxyethylene stearyl ether. The polyoxyethylene stearyl ether may have between about 90 and about 110 oxyethylene units. Preferably, the polyoxyethylene stearyl ether is a polyoxyethylene (100) stearyl ether surfactant (sold under the tradename BRIJ-700). The nonionic surfactants useful in the methods and kits of the invention are commercially available or may be prepared by conventional techniques well-known to those skilled in the art, including those described in, for example, Vaughan Mark Nace, Ed., Nonionic Surfactants: Polyoxyalkylene-Block Copolymers, Surface Science Series Vol. 23; Marcel Dekker: New York, 1996, pages 1 to 30; Meziani, A.; Tourand, D; Zradbra, A; Pulvin, S.; Pezron, I; Clausse, M.; Knunz, W. J. Phys. Chem. B 1997, 101, 3620, the contents of which are incorporated herein by reference.

The hydrophilic/lipophilic character or balance (HLB) value of a surfactant may have an effect on the utility of the surfactant for a Mg-ISE. HLB values range from 0 to 20 where 0 represents no lipophilic character and 20 represents a high lipophilic character. A higher HLB value may result in increased precision and accuracy and lower limits of detection. The polyoxyethylene may have an HLB value that indicates that the surfactant is lipophilic. For example, in certain embodiments, the polyoxyethylene surfactant may have an HLB value greater than about 18. In certain preferred embodiments, the polyoxyethylene surfactant may have an HLB value greater than about greater than about 18.5. In other embodiments, the polyoxyethylene surfactant may have an HLB value from about 18 to about 20.

Figure 2:
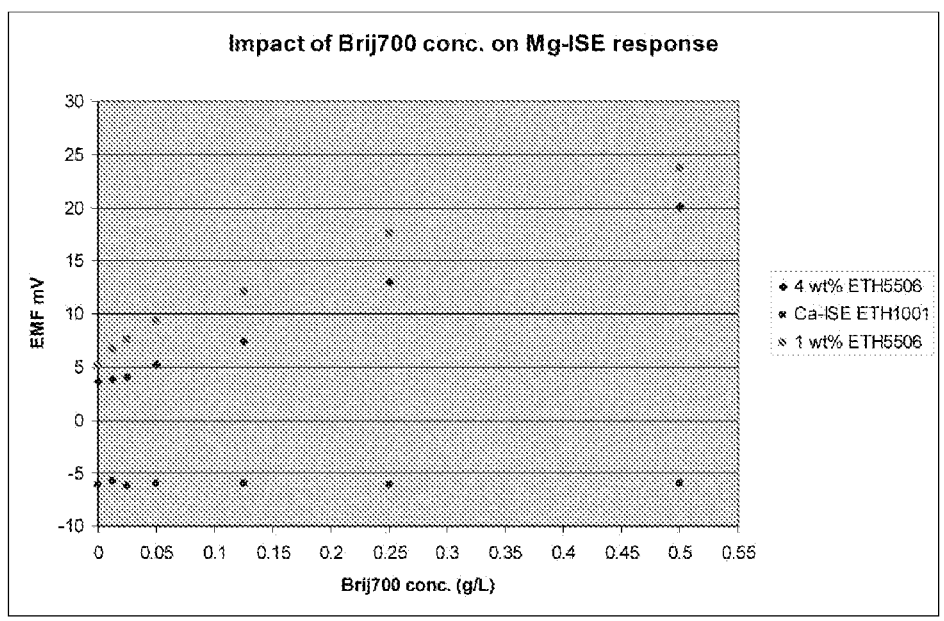
FIG. 2 shows the correlation of polyoxyethylene(100) stearyl ether nonionic surfactant (sold under the tradename BRIJ-700®; CAS No. 9005-00-9) concentration and EMF bias of Mg-ISE and Ca-ISE.

Because polyoxyalkylene surfactants have low CMC levels (e.g. the CMC of BRIJ-700~2.2 g/L), low concentrations may be added to the reagent. For example, the concentration of the polyoxyalkylene nonionic surfactant may be between about 0.010 g/L and about 2.20 g/L. In certain embodiments, the concentration of the polyoxyalkylene nonionic surfactant may be between about 0.010 g/L and about 1.0 g/L, or between about 0.010 g/L and about 0.50 g/L, or between about 0.010 g/L and about 0.25 g/L, or between about 0.010 g/L and about 0.075 g/L. In other embodiments, the concentration of the polyoxyalkylene nonionic surfactant may be between about 0.010 g/L and about 0.050 g/L. As shown in FIGS. 1 and 2, an increase in the concentration of the polyoxyalkylene nonionic surfactant, results in an increased EMF shift. As such, if a lower limit of detection is desired, a lower concentration of polyoxyalkylene may be suitable. Where lower limits of detection are not desired, higher concentrations of polyoxyalkylene nonionic surfactants may be suitable.

In certain embodiments, the EMF shift bias of the Mg-ISE may be reduced to about 10 mV. In other embodiments, the EMF shift bias may be reduced to less than about 10 mV. In certain embodiments, the EMF shift bias may be reduced to less than about 7 mV, or, for example, less than about 5 mV. In yet other embodiments, the EMF shift bias may be reduced to less than about 3, mV, or, for example, less than about 1 mV. A reduced EMF shift bias may allow for lower limits of detection of magnesium ions. Lower detection limits may be suitable when the levels of magnesium ion in a sample are small, for example, in biological samples. Suitable biological samples may include a blood composition, urine, feces, muscle, tissue, saliva, or any other biological sample containing magnesium ions. In a preferred embodiment, the biological sample is a blood composition.

Certain aspects of the present invention may be directed to a method comprising the steps of contacting a magnesium ion selective electrode with a composition comprising a polyoxyalkylene nonionic surfactant, wherein the polyoxyalkylene nonionic surfactant has an HLB greater than about 18; and measuring a biologically relevant level of a blood electrolyte in a blood composition with the electrode. The blood composition may be whole blood, serum, or plasma. In certain embodiments, methods are directed to detecting small amounts of magnesium ion, for example, in biological samples. A biologically relevant amount of magnesium ion may be between about 0.1 mM and about 1.5 mM. In other embodiments, a biologically relevant amount of magnesium ion may be between about 0.1 mM and about 1.0 mM or between about 0.3 mM and about 0.7 mM.

The use of a polyoxyalkylene nonionic surfactant having an HLB greater than about 18 allows for the opportunity to incorporate a Mg-ISE into a clinical diagnostic instrument for the detection of $Mg^{2+}$ along with several other analytes. The clinical diagnostic instrument may also include ISEs suitable for the analysis of analytes such as calcium ion, potassium ion, sodium ion, and chloride ion. The polyoxyalkylene non-ionic surfactant having an HLB greater than about 18 may be included in all or some of the reagents utilized for the analysis of several analytes, including magnesium ions. The reagent may be a calibration reagent, a slope reagent, a wash reagent or a QC reagent, among others. The reagents may be included in a kit further comprising a magnesium ion selective electrode and instructions for use of the reagents and electrode.

The present invention is further defined in the following Examples, in which all parts and percentages are by weight, unless otherwise stated. It should be understood that these examples, while indicating preferred embodiments of the invention, are given by way of illustration only. From the above discussion and these examples, one skilled in the art can ascertain the essential characteristics of this invention, and without departing from the spirit and scope thereof, can make various changes and modifications of the invention to adapt it to various usages and conditions.

EXAMPLES

Example 1

Experimental Setup

Reagents and Chemicals

Calibration reagents were prepared with deionized water and contained 150 mM NaCl, 1.0 mM $CaCl_2$ and varying amounts of $MgCl_2$ (0.1, 0.3, 0.5, 0.7, and 1.0 mM). BRIJ-700 (lot#4050-01) was added to the reagents at varying concentrations of 0.5, 0.25, 0.125, 0.05, 0.025 and 0.0125 g/L. A rinse solution of 0.05 mM $MgCl_2$ (I=160 mM adjusted with NaCl) was used to rinse the Mg-ISE surface after each EMF measurement.

Mg-ISE Sensors

Magnesium ISE membranes were cast with 4 wt % (or 1 wt %) ionophore (ETH5506). Additional membrane components are: lipophilic borate salt (potassium tetrakis(4-chlorophenyl)borate, 150 mol % to ionophore ETH 5506), 62 wt % (or 66 wt %) plasticizer (2-nitrophenyl octyl ether) and 32 wt % PVC (plasticizer:PVC=2:1, weight) to form PVC membrane discs. The membrane thickness is about 150 μm. The discs were mounted onto Philips electrode bodies. The internal filling solution was 10 mM $MgCl_2$ (I=160 mM adjusted with NaCl). Ag, AgCl with 3M KCl was used as a reference electrode. The Mg-ISEs were stored in 10 mM $MgCl_2$ (I=160 mM adjusted with NaCl) when not in use.

EMF Measurements

Prior to measurement, the Mg-ISEs were rinsed with a 0.05 mM $MgCl_2$ solution (I=160 mM adjusted with NaCl). The EMF data acquisition was started when the Mg-ISEs read stable mV values in each solution. Before each solution change, the electrodes were rinsed with 0.05 mM $Mg^2$ solution (I=160 mM). All tests were carried out under a constant temperature of 37° C.

Example 2

Effect of Different BRIJ-700 Levels in Consistent Electrolyte Background

In a constant base solution (0.5 mM $Mg^{2+}$, 150 mM $Na^+$ and 1.0 mM $Ca^{2+}$), different concentrations of BRIJ-700 as described in Example 1 were added. Mg-ISE response in these solutions was measured by comparing with a "blank" solution containing no polyoxyethylene(100) stearyl ether nonionic surfactant (sold under the tradename BRIJ-700®; CAS No. 9005-00-9). A Ca-ISE based on ETH1001 was simultaneously tested with two Mg-ISEs (1 wt % and 4 wt % ETH5506). The responses of both the Mg-ISEs and the Ca-ISE were measured. As shown in FIGS. 1 and 2, a quantitative relationship exists between the BRIJ-700 concentration and its impact on EMF off-set of Mg-ISEs. Unlike the Ca-ISE, the Mg-ISEs show significant sensitivity to the concentration of BRIJ-700. This may be the result of surfactant molecules penetrating into the PVC membrane and competing with ionophores in the PVC membrane regarding the binding affinity to the target ions, $Mg^{2+}$. The higher concentration of BRIJ-700 leads to stronger binding between surfactant and target ion.

Polyoxyethylene(100) stearyl ether nonionic surfactant (sold under the tradename BRIJ-700®; CAS No. 9005-00-9) does not show any influence to the Ca-ISE response while it does show an effect on Mg-ISE response. Indeed, the Mg-ISE with the higher ionophore level shows less influence of BRIJ-700, especially at the lower level in solution (<0.05 g/L). As indicated in FIG. 1, the Mg-ISE with 4 wt % ionophore ETH5506 showed less sensitive to BRIJ-700 concentration than the Mg-ISE with 1 wt % ionophore. This may be explained by the fact that higher concentration of ionophore in the sensor membrane can relatively enhance the resistance toward surfactant molecules in reagent solutions.

Example 3

Measurements of Mg Ions in Biologically Relevant Concentrations

Figure 3:
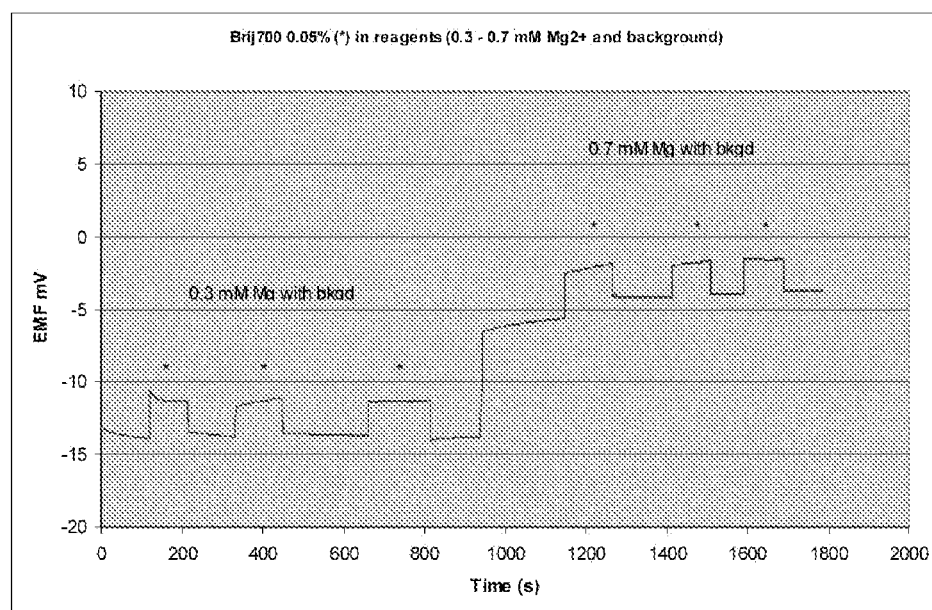
FIG. 3 shows polyoxyethylene(100) stearyl ether nonionic surfactant (sold under the tradename BRIJ-700®; CAS No. 9005-00-9) impact on MG-ISE response in a physiological $Mg^{2+}$ range.

The impact of BRIJ-700 on Mg-ISE response to $Mg^{2+}$ over a physiological normal range (0.3-0.7 mM) was studied. As shown in FIG. 3, 0.05% BRIJ-700 addition in reagents can lead to significant mV bias of Mg-ISE response (~+4 mV). At the level of 0.025% BRIJ-700 in reagents (not shown), such mV bias shrinks to ~+1 mV. In this range, the mV bias is parallel mV bias that can be mathematically corrected. FIG. 3 also shows that the mV bias of BRIJ-700 on Mg-ISEs can easily be removed when a fresh reagent without BRIJ-700 is used.

This is very different from the feature of BRIJ-35 with Mg-ISEs as reported in previous publications. BRIJ-35 and TRITON X-100 cause very high mV bias on Mg-ISE response (>100 mV in 0.1% surfactant) and such mV bias can only be removed over several hours or even days. This is one of the reasons that IFCC recommends using MEGA instead of BRIJ-35.

Figure 4:
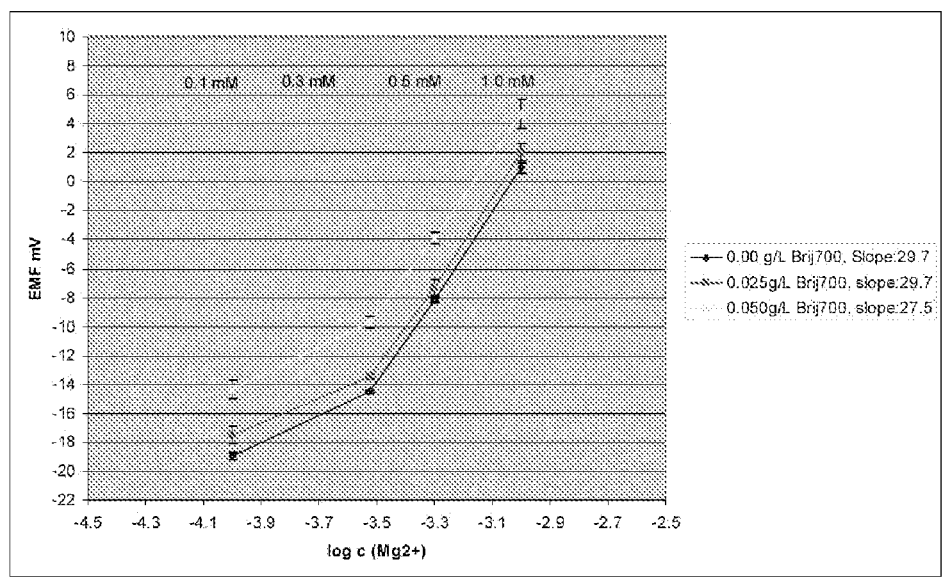
FIG. 4 shows the influence of polyoxyethylene(100) stearyl ether nonionic surfactant (sold under the tradename BRIJ-700®; CAS No. 9005-00-9) concentration on Mg-ISE response in a physiological $Mg^{2+}$ range.

FIG. 4 shows EMF bias over an extended physiological range from 0.1 to 1.0 mM $Mg^{2+}$. The influence of BRIJ-700 on a Mg-ISE's mV bias was studied. Four levels of $Mg^{2+}$ (0.1, 0.3, 0.5, and 1.0 mM) in electrolyte background were tested with and without the addition of BRIJ-700 (0.00%, 0.025%, and 0.05%). The test was performed in triplicate. At the lower $Mg^{2+}$ range (e.g. 0.1 mM), the mV bias was somewhat larger than at higher concentrations of $Mg^{2+}$. The EMF of Mg-ISEs in three solution series shows parallel shift along with the increase of BRIJ-700 concentration. In the range from 0.3 to 1.0 mM, the addition of 0.025% BRIJ-700 in reagents causes very minor mV bias which is as small as 1 mV.

TABLE 1

| BRIJ-700 influence to Mg-ISE in physiological normal $Mg^{2+}$ range | | | | | | | |
|---|---|---|---|---|---|---|---|
| $c(Mg^{2+})$ | | 0.00% BRIJ-700 | | 0.025% BRIJ-700 | | 0.05% BRIJ-700 | |
| M | $logc(Mg^{2+})$ | mV | Sd (n = 3) | mV | sd (n = 3) | mV | sd (n = 3) |
| 0.0001 | −4.00 | −18.93 | 0.241 | −17.49 | 0.568 | −14.34 | 0.673 |
| 0.0003 | −3.52 | −14.50 | 0.069 | −13.48 | 0.152 | −9.69 | 0.403 |
| 0.0005 | −3.30 | −8.20 | 0.142 | −7.32 | 0.561 | −3.91 | 0.406 |
| 0.0010 | −3.00 | +1.01 | 0.405 | +1.99 | 0.700 | +4.68 | 1.01 |
| Slope* | mV/d 37 C. | 29.73 | | 29.67 | | 27.54 | |

*The slope is calculated in the linear range of 0.3 mM to 1.0 mM of $Mg^{2+}$ (I = 160 mM)

Since all tests were under the temperature of 37° C., the theoretical Nernstian slope of Mg-ISEs is 30.76 mV/dec. With the addition of BRIJ-700 at 0.025%, the response slope keeps the similar level as in reagents without BRIJ-700. However, when 0.05% BRIJ-700 is added, the response slope drops to 27.54 mV/dec (which is about 7.5% drop in slope).

Table 2 shows that parallel mV bias of Mg-ISE in different levels of BRIJ-700 can be corrected in a calculation algorithm for testing $Mg^{2+}$ in sample. At the level of 0.025 g/L BRIJ-700, the mV bias is about +1 mV comparing to the level of 0.00 g/L BRIJ-700. At the level of 0.05 g/L, the mV bias is about +4 mV.

TABLE 2

| mV bias of Mg-ISE in reagents containing different levels of BRIJ-700 | | | | |
|---|---|---|---|---|
| c(Mg) M | logc(Mg) | Δ (0.025%-0.00%) BRIJ-700 mV | Δ (0.05%-0.00%) BRIJ-700 mV | Δ (0.05%-0.025%) BRIJ-700 mV |
| 0.0001 | −4.00 | 1.45 | 4.60 | 3.15 |
| 0.0003 | −3.52 | 1.02 | 4.81 | 3.79 |
| 0.0005 | −3.30 | 0.87 | 4.28 | 3.41 |
| 0.0010 | −3.00 | 0.98 | 3.66 | 2.68 |

If 0.025 g/L level BRIJ-700 in reagents could maintain adequate foaming effect for the instrument fluidic requirements, the interference to Mg-ISE can be minimized accordingly. The mV bias can be reduced as small as 0.1 mV over all physiological $Mg^{2+}$ range and the response slope is almost not affected.

Example 4

Response Signal Shift of Mg ISE

Figure 5:
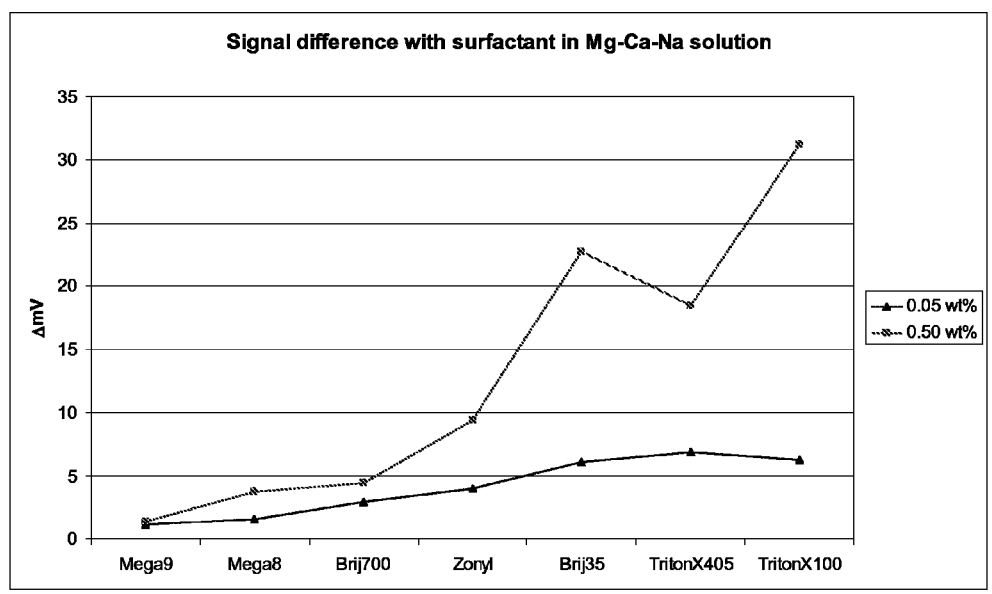
FIG. 5 shows the response signal shift of Mg ISE with seven different surfactants.

The response signal shifts (ΔmV) of Mg ISE with seven different surfactants were studied (see FIG. 5). Each surfactant was tested with two concentration levels of 0.05 wt % and 0.5 wt % in solution ($Mg^{2+}$ 0.5 mM, $Ca^{2+}$, 1.0 mM, $Na^{30}$ 150 mM). Mega-8, Mega-9 and Brij700 showed less influence on Mg ISE response signal and the mV shift (ΔmV<5 mV at 0.5 wt %). Brij 35, Triton 405 and Triton 100 showed strong impact on Mg ISE response signal (ΔmV>5 mV at 0.05 wt %). This means Brij35, TritoX100 and TritonX405 were not suitable to be used for Mg ISE.

When ranges are used herein for physical properties, such as molecular weight, or chemical properties, such as chemical formulae, all combinations, and subcombinations of ranges specific embodiments therein are intended to be included.

The disclosures of each patent, patent application, and publication cited or described in this document are hereby incorporated herein by reference, in their entirety.

Those skilled in the art will appreciate that numerous changes and modifications can be made to the preferred embodiments of the invention and that such changes and modifications can be made without departing from the spirit of the invention. It is, therefore, intended that the appended claims cover all such equivalent variations as fall within the true spirit and scope of the invention.

What is claimed:

1. A method of reducing the shift in electromotive force (EMF) bias in a magnesium ion selective electrode, comprising the step of:
  contacting said electrode with a composition comprising a polyoxyalkylene nonionic surfactant;
  wherein said polyoxyalkylene nonionic surfactant has a hydrophilic-lipophilic balance (HLB) greater than about 18.

2. The method of claim 1, wherein said shift in EMF bias is less than about 10 mV.

3. The method of claim 1, wherein said polyoxyalkylene nonionic surfactant is a polyoxyethylene nonionic surfactant.

4. The method of claim 3, wherein said polyoxyethylene nonionic surfactant is a polyoxyethylene stearyl ether surfactant having between about 90 and about 110 oxyethylene units.

5. The method of claim 4, wherein said polyoxyethylene stearyl ether surfactant having between about 90 and about 110 oxyethylene units is a polyoxyethylene (100) stearyl ether surfactant.

6. The method of claim 1, wherein the concentration of said polyoxyalkylene nonionic surfactant is between about 0.010 g/L and about 2.20 g/L.

7. The method of claim 6, wherein the concentration of said polyoxyalkylene nonionic surfactant is between about 0.010 g/L and about 1.00 g/L.

8. The method of claim 7, wherein the concentration of said polyoxyalkylene nonionic surfactant is between about 0.010 g/L and about 0.50 g/L.

9. The method of claim 8, wherein the concentration of said polyoxyalkylene nonionic surfactant is between about 0.010 g/L and about 0.25 g/L.

10. The method of claim 9, wherein the concentration of said polyoxyalkylene nonionic surfactant is between about 0.010 g/L and about 0.075 g/L.

11. The method of claim 10, wherein the concentration of said polyoxyalkylene nonionic surfactant is between about 0.010 g/L and about 0.050 g/L.

12. A method, comprising the steps of:
   contacting a magnesium ion selective electrode with a composition comprising a polyoxyalkylene nonionic surfactant,
   wherein said polyoxyalkylene nonionic surfactant has a hydrophilic-lipophilic balance (HLB) greater than about 18; and
   measuring a biologically relevant level of magnesium ion in a blood composition with said electrode.

13. The method of claim 12, wherein said polyoxyalkylene nonionic surfactant causes less than about a 10 mV shift in EMF bias in said magnesium ion selective electrode.

14. The method of claim 12, wherein said polyoxyalkylene nonionic surfactant is a polyoxyethylene nonionic surfactant.

15. The method of claim 14, wherein said polyoxyethylene nonionic surfactant is a polyoxyethylene stearyl ether surfactant having between about 90 and about 110 oxyethylene units.

16. The method of claim 15, wherein said polyoxyethylene stearyl ether surfactant having between about 90 and about 110 oxyethylene units is a polyoxyethylene (100) stearyl ether surfactant.

17. The method of claim 12, wherein said blood composition is whole blood, serum, or plasma.

18. The method of claim 12, wherein said biologically relevant level of said blood electrolyte is between about 0.1 mM and about 1.0 mM.

19. The method of claim 18, wherein said biologically relevant level of said blood electrolyte is between about 0.3 mM and about 0.7 mM.

20. The method of claim 12, wherein the concentration of said polyoxyalkylene nonionic surfactant is between about 0.010 g/L and about 2.20 g/L.

21. The method of claim 20, wherein the concentration of said polyoxyalkylene nonionic surfactant is between about 0.010 g/L and about 1.00 g/L.

22. The method of claim 21, wherein the concentration of said polyoxyalkylene nonionic surfactant is between about 0.010 g/L and about 0.50 g/L.

23. The method of claim 22, wherein the concentration of said polyoxyalkylene nonionic surfactant is between about 0.010 g/L and about 0.25 g/L.

24. The method of claim 23, wherein the concentration of said polyoxyalkylene nonionic surfactant is between about 0.010 g/L and about 0.075 g/L.

25. The method of claim 24, wherein the concentration of said polyoxyalkylene nonionic surfactant is between about 0.010 g/L and about 0.050 g/L.

26. A kit comprising:
   a magnesium ion selective electrode;
   a calibration reagent comprising a polyoxyalkylene nonionic surfactant,
   wherein said polyoxyalkylene nonionic surfactant has a hydrophilic-lipophilic balance (HLB) greater than about 18;
   a wash reagent comprising a polyoxyalkylene nonionic surfactant,
   wherein said polyoxyalkylene nonionic surfactant has a hydrophilic-lipophilic balance (HLB) greater than about 18;
   a slope reagent comprising a polyoxyalkylene nonionic surfactant,
   wherein said polyoxyalkylene nonionic surfactant has a hydrophilic-lipophilic balance (HLB) greater than about 18; and
   instructions for rinsing, calibrating, and operating the electrode.

27. The kit of claim 26, wherein said polyoxyalkylene nonionic surfactant is a polyoxyethylene nonionic surfactant.

28. The kit of claim 27, wherein said polyoxyethylene nonionic surfactant is a polyoxyethylene stearyl ether surfactant having between about 90 and about 110 oxyethylene units.

29. The kit of claim 28, wherein said polyoxyethylene stearyl ether surfactant having between about 90 and about 110 oxyethylene units is a polyoxyethylene (100) stearyl ether surfactant.

30. The kit of claim 26, wherein the concentration of said polyoxyalkylene nonionic surfactant is between about 0.010 g/L and about 2.20 g/L.

31. The kit of claim 30, wherein the concentration of said polyoxyalkylene nonionic surfactant is between about 0.010 g/L and about 1.00 g/L.

32. The kit of claim 31, wherein the concentration of said polyoxyalkylene nonionic surfactant is between about 0.010 g/L and about 0.50 g/L.

33. The kit of claim 32, wherein the concentration of said polyoxyalkylene nonionic surfactant is between about 0.010 g/L and about 0.25 g/L.

34. The kit of claim 33, wherein the concentration of said polyoxyalkylene nonionic surfactant is between about 0.010 g/L and about 0.075 g/L.

35. The kit of claim 34, wherein the concentration of said polyoxyalkylene nonionic surfactant is between about 0.010 g/L and about 0.050 g/L.

* * * * *